United States Patent
Kim et al.

(10) Patent No.: US 11,266,706 B2
(45) Date of Patent: Mar. 8, 2022

(54) METHOD FOR PREVENTING OR ALLEVIATING LIPID METABOLISM DISORDERS USING COMPOSITION CONTAINING GREEN TEA EXTRACT WITH INCREASED SPECIFIC INGREDIENT CONTENT

(71) Applicant: AMOREPACIFIC CORPORATION, Seoul (KR)

(72) Inventors: Ayoung Kim, Yongin-si (KR); Hyun Woo Jeong, Yongin-si (KR); Yong-Deog Hong, Yongin-si (KR); Jeong-Kee Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/760,787

(22) PCT Filed: Aug. 9, 2018

(86) PCT No.: PCT/KR2018/009069
§ 371 (c)(1),
(2) Date: Apr. 30, 2020

(87) PCT Pub. No.: WO2019/088412
PCT Pub. Date: May 9, 2019

(65) Prior Publication Data
US 2020/0323942 A1     Oct. 15, 2020

(30) Foreign Application Priority Data

Oct. 30, 2017 (KR) .................. 10-2017-0142215

(51) Int. Cl.
| | | |
|---|---|---|
| *A61K 36/82* | (2006.01) | |
| *A61P 1/16* | (2006.01) | |
| *A61P 3/04* | (2006.01) | |
| *A61P 3/06* | (2006.01) | |
| *A61K 9/00* | (2006.01) | |

(52) U.S. Cl.
CPC ............ *A61K 36/82* (2013.01); *A61K 9/0053* (2013.01); *A61P 1/16* (2018.01); *A61P 3/04* (2018.01); *A61P 3/06* (2018.01); *A61K 2236/331* (2013.01); *A61K 2236/333* (2013.01)

(58) Field of Classification Search
None
See application file for complete search history.

(56) References Cited

U.S. PATENT DOCUMENTS

| | | | |
|---|---|---|---|
| 2013/0259855 A1 | 10/2013 | Kim et al. | |
| 2015/0374019 A1* | 12/2015 | Dorr | A61K 31/353 |
| | | | 426/2 |
| 2016/0213731 A1* | 7/2016 | Kim | A61K 36/48 |
| 2017/0156361 A1 | 6/2017 | Tachibana | |
| 2020/0397746 A1* | 12/2020 | Jeong | A61K 9/4858 |

FOREIGN PATENT DOCUMENTS

| | | | |
|---|---|---|---|
| CN | 103327995 A | | 9/2013 |
| CN | 106132427 A | | 11/2016 |
| JP | 2006-083106 A | * | 3/2006 |
| JP | 2006-83106 A | | 3/2006 |
| JP | 2006-131512 A | | 5/2006 |
| KR | 10-2005-0093894 A | | 9/2005 |
| KR | 10-2008-0066115 A | | 7/2008 |
| KR | 10-2012-0064299 A | | 6/2012 |
| KR | 10-2014-0103488 A | | 8/2014 |
| KR | 10-1685876 B1 | | 12/2016 |
| WO | 2014/083172 A1 | | 6/2014 |
| WO | 2015/199169 A1 | | 12/2015 |

OTHER PUBLICATIONS

Saeed, M. et al. Green Tea and L-Theanine: Medicinal Values and Beneficial Applications in Humans. Biomedicine & Pharmacotherapy 95:1260-1275, 2017. (Year: 2017).*
Cho, D. et al. Gallocatechin Gallate Containing Fermented Green Tea Extract . . . J of Medicinal Food 22(8)779-788, 2019. (Year: 2019).*
Ikeda, I. et al. Dietary Gallate Esters of Tea Catechins Reduce Deposition of Visceral Fat . . . Bioscience, Biotechnology, and Biochemistry 69(5)1049-1053, 2005. (Year: 2005).*
Ikda I. Multifunctional Effects of Green Tea Catechins on Prevention of the Metabolic Syndrome. Asia Pacific J Clinical Nutrition 17(S1)273-274, 2008. (Year: 2008).*
International Search Report from International Application No. PCT/KR2018/009069, dated Feb. 8, 2019.
Written Opinion from International Application No. PCT/KR2018/009069, dated Feb. 8, 2019.
Ge Bin et al., "Therapeutic effect of epigallocatechin gallate on hyperlipidemic fatty liver in rats", Chinese Pharmacological Bulletin, vol. 25(4): 510-514 (2009).
Wang Jialu et al., "Study on effect of (-)-epigallocatechin-3-gallate for improving body weight and related metabolism in rats fed with high-fat diet", J Intern Med Concepts Pract, vol. 11(5): 309-312 (2016).
Office Action for Chinese Patent Application No. 201880071484.5 (dated Aug. 5, 2021).

* cited by examiner

*Primary Examiner* — Ralph J Gitomer
(74) *Attorney, Agent, or Firm* — Merchant & Gould P.C.

(57) ABSTRACT

The present specification relates to a composition containing a tea extract with an increased specific ingredient content for prevention or alleviation of lipid metabolism disorders. The use of a preparation method and a composition according to the present specification can effectively prevent and treat lipid metabolism disorders including obesity without side effects, thereby meeting related demands and promoting the development of corresponding industries.

12 Claims, 8 Drawing Sheets

METHOD FOR PREVENTING OR ALLEVIATING LIPID METABOLISM DISORDERS USING COMPOSITION CONTAINING GREEN TEA EXTRACT WITH INCREASED SPECIFIC INGREDIENT CONTENT

TECHNICAL FIELD

The present specification relates to a composition containing a tea extract with an increased specific ingredient content for prevention or alleviation of lipid metabolism disorders.

CROSS-REFERENCE TO RELATED APPLICATIONS

This application is a National Stage Application of International Application No. PCT/KR2018/009069 filed Aug. 9, 2018, which claims priority to Korean Patent Application No. 10-2017-0142215, filed on Oct. 30, 2017, and all the benefits accruing therefrom under 35 U.S.C. § 119, the contents of which in its entirety are herein incorporated by reference.

BACKGROUND ART

Obesity occurs when fat tissues in the body are in excess and the amount of calorie ingested is greater than the amount of calorie consumed, and also occurs for various causes such as mental and social factors, genetics, diseases, and drugs. According to the World Health Organization (WHO) in 2010, it was reported that the overweight adult population was estimated at about 1.6 billion worldwide and the number of obese people was estimated at about 400 million, and 2.6 million people die from obesity or overweight every year. Even in Korea, according to the reports by the Ministry of Health and Welfare and the Korea Centers for Disease Control & Prevention, adult obesity rates have continued to increase, and were shown to be 30% (36.3% male, 24.8% female) based on the year 2010. As described above, the obese population continues to increase worldwide, and the burden of medical expenses is also increasing. Obesity has become one of the most common diseases for modern people.

Obesity may be managed through lifestyle changes such as behavioral therapy along with dietary therapy and regular exercise, and drugs such as appetite suppressants and fat absorption inhibitors. Since obesity is a chronic disease, long-term use of medication is required when drug therapy is attempted, and currently, products that have been approved for long-term use in Korea for three or more months include sibutramine as an appetite suppressant and orlistat as a lipolytic enzyme inhibitor. However, since a considerable number of these drugs for treating obesity are psychotropic drugs that act on the central nervous system to regulate appetite, these drugs are accompanied by side effects such as headache and vomiting, and have problems such as concerns of abuse. As the demand for drugs and foods capable of treating obesity effectively without side effects continues to increase, there is an urgent need for finding products derived from nature, which are capable of preventing and treating obesity.

SUMMARY OF INVENTION

Technical Problem

An object of the present specification is to find an extract and a composition derived from natural products capable of preventing and treating lipid metabolism disorders including obesity.

Solution to Problem

To solve the object, the present specification provides a composition for prevention or alleviation of lipid metabolism disorders, containing a green tea extract, as an active ingredient, comprising 1 to 5 wt % of (−)-gallocatechin gallate (GCG), 0.1 to 0.5 wt % of (−)-catechin gallate (CG), and 0.8 to 4 wt % of (−)-epigallocatechin gallate (EGCG) based on a total weight of the composition.

Further, the present specification provides a method for preparing a composition for prevention or alleviation of lipid metabolism disorders, the method including: (1) adjusting moisture in green tea and inoculating a *Bacillus* genus strain to the green tea; (2) maintaining the inoculated green tea at 40 to 60° C.; (3) aging the inoculated green tea at 70 to 80° C.; and (4) adding one or more of water and C1 to C6 alcohols thereto and extracting a green tea extract at 50° C. to 80° C.

Furthermore, the present specification also provides a method for maximizing a content of (−)-gallocatechin gallate (GCG) in a green tea extract.

Advantageous Effects of Invention

Since lipid metabolism disorders including obesity can be effectively prevented and treated without side effects using a preparation method and a composition according to an aspect of the present invention, the related demand will be satisfied and the industry will be developed.

DESCRIPTION OF EMBODIMENTS

Figure 1:
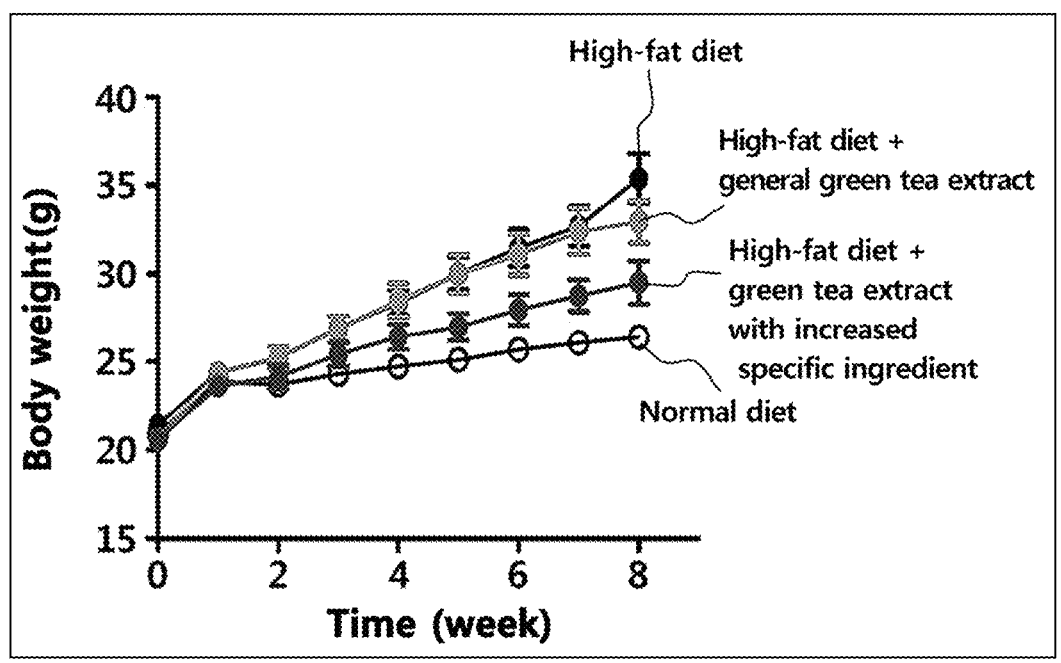
FIG. 1 illustrates the effect of a green tea extract with an increased specific ingredient content according to an aspect of the present invention on the suppression of body weight gain in comparison with those of other groups.

In the present specification, "green tea extract" includes an extract extracted from tea (*Camellia sinensis*), which is an evergreen shrub belonging to the tea family, regardless of the extraction method, extraction solvent, extracted ingredient, or form of extract, or an extract extracted from tea leaves inoculated with *Bacillus subtilis* spp. and fermented, and includes a fraction obtained by fractionating the extracted extract with a specific solvent. The tea may include one or more selected from the group consisting of leaves, flowers, stems, fruits, roots, stems, and root cores of tea plant, and may preferably be leaves. Further, the form of extract may be preferably in a powder form. The extraction or fractionation may be performed using water, an organic solvent, or a mixed solvent thereof. The organic solvent may be an alcohol, isopropanol, acetone, hexane, ethyl acetate, carbon dioxide, or a mixed solvent of two or more thereof, but is not limited thereto, and an active ingredient of green tea may be extracted or fractionated at room temperature or by heating under the condition that the active ingredient is not destroyed or is minimized. The alcohol may be a $C_1$ to $C_6$ lower alcohol. The number or method of extraction or fractionation is not particularly limited, and for example, it is possible to use a method such as cold precipitation extraction, ultrasonic extraction, reflux cooling extraction, and hot-water extraction, and preferably, the active ingredient may be extracted or fractionated by cold precipitation or heating and filtered, and then the filtrate may be concentrated under reduced pressure to obtain the green tea extract of the present invention.

In the present specification, "pharmaceutically acceptable" means that it is recognized that one can be used for an animal, more specifically humans by avoiding significant toxic effects when being used in conventional medicinal dosages as being capable of being approved or as being approved by the government or a regulatory agency equivalent thereto or as being enumerated in the pharmacopeia or as being described in other general pharmacopeias.

In the present specification, "pharmaceutically acceptable salt" means a salt according to an aspect of the present invention which is pharmaceutically acceptable and has the desired pharmacological activity of a parent compound.

In the present specification, "total catechin" means a total sum of four epicatechins (epigallocatechin (EGC), (–) epicatechin (EC), (–)-epigallocatechin gallate (EGCG), and epicatechin 3-O-gallate (ECG)).

An aspect of the present invention may be a composition for prevention or alleviation of lipid metabolism disorders, containing a green tea extract, as an active ingredient, comprising 1 to 5 wt % of (–)-gallocatechin gallate (GCG), 0.1 to 0.5 wt % of (–)-catechin gallate (CG), and 0.8 to 4 wt % of (–)-epigallocatechin gallate (EGCG) based on a total weight of the composition.

Another aspect of the present invention may relate to a method for preventing or alleviating lipid metabolism disorders, the method including: administering, to a subject, a composition containing a green tea extract, as an active ingredient, comprising 1 to 5 wt % of (–)-gallocatechin gallate (GCG), 0.1 to 0.5 wt % of (–)-catechin gallate (CG), and 0.8 to 4 wt % of (–)-epigallocatechin gallate (EGCG) based on a total weight of the composition.

Still another aspect of the present invention may relate to a use of a green tea extract comprising 1 to 5 wt % of (–)-gallocatechin gallate (GCG), 0.1 to 0.5 wt % of (–)-catechin gallate (CG), and 0.8 to 4 wt % of (–)-epigallocatechin gallate (EGCG) based on a total weight of a composition for use in the preparation of the composition for prevention or alleviation of lipid metabolism disorders.

As an exemplary embodiment, a content of the GCG may be 1 wt % or more, 2 wt % or more, 2.9 wt % or more, 2.92 wt % or more, 3 wt % or more, 3.1 wt % or more, 3.12 wt % or more, 3.15 wt % or more, 3.3 wt % or more, 3.5 wt % or more, 3.8 wt % or more, 4.0 wt % or more, 4.2 wt % or more, 4.4 wt % or more, 4.6 wt % or more, or 4.8 wt % or more. As another exemplary embodiment, a content of the GCG may be 5 wt % or less, 4.8 wt % or less, 4.6 wt % or less, 4.4 wt % or less, 4.2 wt % or less, 4 wt % or less, 3.5 wt % or less, 3.4 wt % or less, 3.3 wt % or less, 3.2 wt % or less, 3.12 wt % or less, 3.1 wt % or less, 2.95 wt % or less, 2.92 wt % or less, 2.9 wt % or less, 2.51 wt % or less, 2.4 wt % or less, 2.2 wt % or less, 1.5 wt % or less, 1.8 wt % or less, 1.5 wt % or less, or 1.3 wt % or less.

As an exemplary embodiment, a content of the CG may be 0.1 wt % or more, 0.2 wt % or more, 0.3 wt % or more, 0.31 wt % or more, 0.35 wt % or more, 0.36 wt % or more, 0.38 wt % or more, 0.39 wt % or more, 0.4 wt % or more, 0.42 wt % or more, 0.45 wt % or more, or 0.48 wt % or more. As another exemplary embodiment, a content of the CG may be 0.5 wt % or less, 0.48 wt % or less, 0.46 wt % or less, 0.44 wt % or less, 0.42 wt % or less, 0.4 wt % or less, 0.39 wt % or less, 0.38 wt % or less, 0.36 wt % or less, 0.35 wt % or less, 0.32 wt % or less, 0.3 wt % or less, 0.29 wt % or less, 0.28 wt % or less, 0.25 wt % or less, 0.2 wt % or less, or 0.15 wt % or less.

As an exemplary embodiment, a content of the EGCG may be 0.8 wt % or more, 0.9 wt % or more, 1.0 wt % or more, 1.1 wt % or more, 1.2 wt % or more, 1.3 wt % or more, 1.4 wt % or more, 1.5 wt % or more, 1.8 wt % or more, 2 wt % or more, 2.2 wt % or more, 2.4 wt % or more, 2.5 wt % or more, 2.6 wt % or more, 2.8 wt % or more, 3 wt % or more, 3.2 wt % or more, 3.4 wt % or more, 3.6 wt % or more, 3.7 wt % or more, 3.8 wt % or more, or 3.9 wt % or more. As another exemplary embodiment, a content of the EGCG may be 4 wt % or less, 3.9 wt % or less, 3.8 wt % or less, 3.7 wt % or less, 3.6 wt % or less, 3.4 wt % or less, 3.2 wt % or less, 3 wt % or less, 2.8 wt % or less, 2.6 wt % or less, 2.4 wt % or less, 2.2 wt % or less, 2 wt % or less, 1.8 wt % or less, 1.6 wt % or less, 1.4 wt % or less, 1.2 wt % or less, 1.0 wt % or less, or 0.9 wt % or less.

As an exemplary embodiment, a total catechin content in the composition may be 10 wt % or less, 8 wt % or less, 7.5 wt % or less, 7.45 wt % or less, or 7 wt % or less based on the total weight of the composition. As another exemplary embodiment, the total catechin content may be 6 wt % or more, 6.5 wt % or more, 7 wt % or more, 7.4 wt % or more, 7.44 wt % or more, 7.5 wt % or more, 8 wt % or more, or 9 wt % or more.

When the contents of the GCG, CG, EGCG, and total catechin are out of the above ranges, the effects of the following experimental examples are not exhibited, or the effect level becomes similar to that of a general green tea extract.

Figure 6:
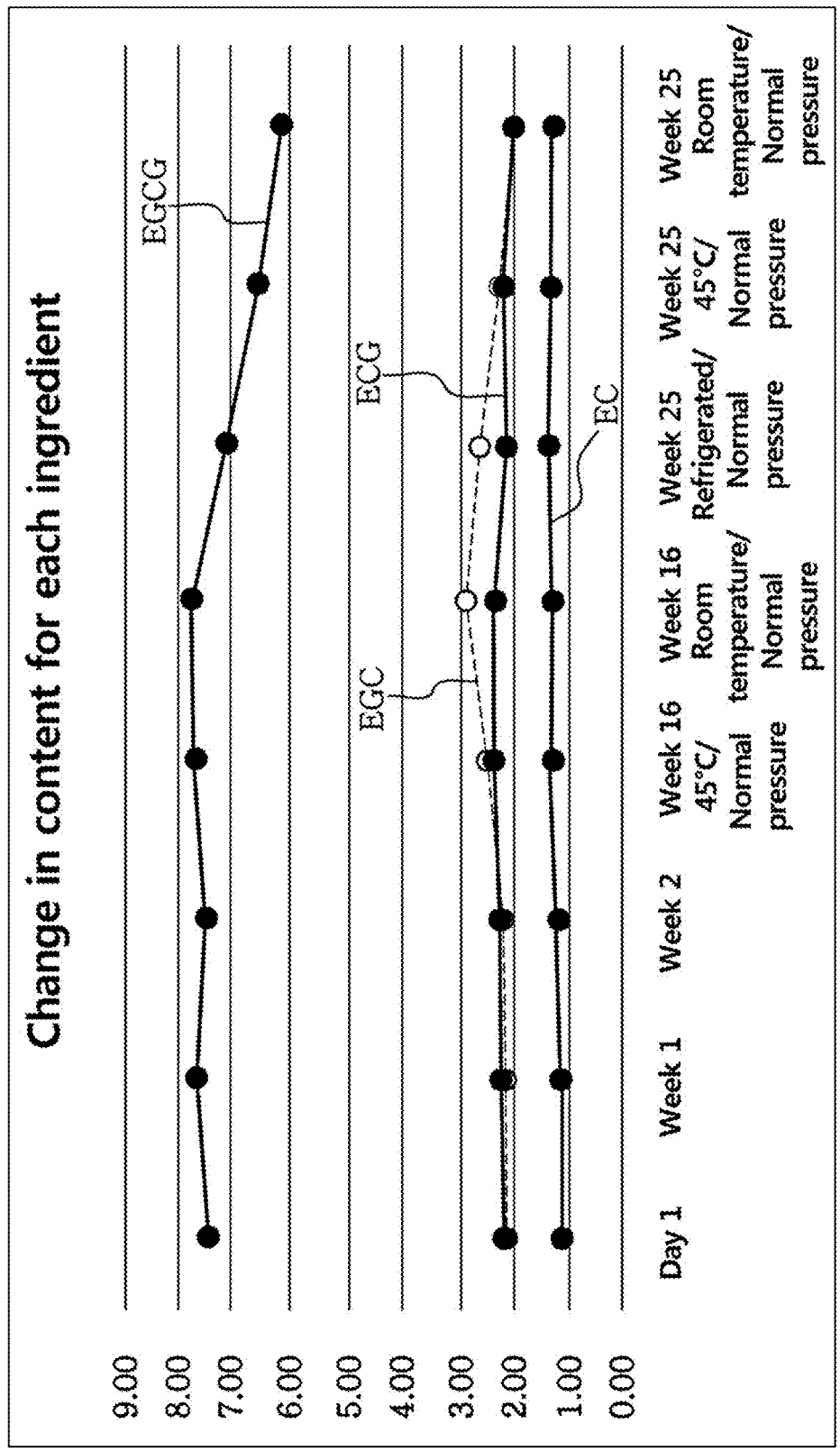
FIG. 6 illustrates the changes in content of a green tea extract with an increased specific ingredient content according to an aspect of the present invention for each ingredient and condition.

The content of the total catechin may have a stability problem due to EGCG, which loses stability over time, and therefore, it is likely to be difficult to maintain the efficacy based on the total catechin content (see FIG. 6). An extract according to an aspect of the present invention relates to a green tea extract that exhibits a far superior effect even though the total catechin content is small, and showed a remarkably better result in terms of effect for lipid metabolism disorders than existing green tea extracts by maximizing the contents of GCG ingredients which have not been confirmed from existing general green tea extracts (see the following experimental examples).

In an aspect, a weight ratio of EGCG:GCG in the extract may be 2:0.5 to 12.5 or more. As an exemplary embodiment, the weight ratio may be 2:0.5 or more, 2:0.7 or more, 2:0.9 or more, 2:1 or more, 2:1.2 or more, 2:1.4 or more, 2:1.5 or more, 2:1.6 or more, 2:1.7 or more, 2:1.8 or more, 2:2 or more, 2:2.2 or more, 2:2.4 or more, 2:2.6 or more, 2:2.8 or more, 2:3 or more, 2:3.2 or more, 2:3.4 or more, 2:3.6 or more, 2:3.8 or more, 2:4 or more, 2:4.2 or more, 2:4.5 or more, 2:4.8 or more, 2:5 or more, 2:6 or more, 2:7 or more, 2:8 or more, 2:9 or more, 2:10 or more, 2:11 or more, or 2:12 or more. As another exemplary embodiment, the weight ratio may be 2:12.5 or less, 2:12 or less, 2:11 or less, 2:10 or less, 2:9 or less, 2:8 or less, 2:7 or less, 2:6 or less, 2:5.5 or less, 2:5 or less, 2:4.8 or less, 2:4.6 or less, 2:4.4 or less, 2:4.2 or less, 2:4 or less, 2:3.8 or less, 2:3.6 or less, 2:3.4 or less, 2:3.2 or less, 2:3 or less, 2:2.8 or less, 2:2.6 or less, 2:2.4 or less, 2:2.2 or less, 2:2 or less, 2:1.8 or less, 2:1.6 or less, 2:1.4 or less, 2:1.2 or less, 2:1 or less, 2:0.8 or less, or 2:0.6 or less. Preferably, the weight ratio may be 2:1.5 to 5.

In another aspect, a weight ratio of GCG:CG in the extract may be 1:0.02 to 0.3. As an exemplary embodiment, the weight ratio may be 1:0.02 or more, 1:0.03 or more, 1:0.04 or more, 1:0.05 or more, 1:0.08 or more, 1:0.1 or more, 1:0.12 or more, 1:0.15 or more, 1:0.18 or more, 1:0.2 or more, 1:0.23 or more, 1:0.26 or more, or 1:0.28 or more. As another exemplary embodiment, the weight ratio may be 1:0.3 or less, 1:0.28 or less, 1:0.26 or less, 1:0.24 or less, 1:0.22 or less, 1:0.2 or less, 1:0.18 or less, 1:0.16 or less, 1:0.14 or less, 1:0.12 or less, 1:0.1 or less, 1:0.08 or less, 1:0.06 or less, 1:0.04 or less, or 1:0.03 or less. Preferably, the weight ratio may be 1:0.05 to 0.3.

When the weight ratio of EGCG:GCG or the weight ratio of GCG:CG is out of the above range, the following effect of preventing or alleviating lipid metabolism disorders may be insignificant, or may be similar to that of a general green tea extract.

In an aspect, the extract may be an extract extracted one or more times by one or more of water, a C1 to C6 alcohol, and a mixture thereof. As an exemplary embodiment, the alcohol may be ethanol. As another exemplary embodiment, in the case of the mixture, a concentration of the alcohol may be 20% (v/v) or more, 30% (v/v) or more, 40% (v/v) or more, 50% (v/v) or more, 60% (v/v) or more, or 70% (v/v) or more. As still another exemplary embodiment, in the case of the mixture, a concentration of the alcohol may be 80% (v/v) or less, 70% (v/v) or less, 60% (v/v) or less, 50% (v/v) or less, 40% (v/v) or less, or 30% (v/v) or less. When the concentration of the alcohol is out of the above range, the active ingredient in tea may not be sufficiently extracted, or the extracted ingredient may be modified and destroyed.

In another aspect, a content of the extract in the composition may be 1 wt % to 100 wt % based on the dry weight. As an exemplary embodiment, a content of the extract may be 1 wt % or more, 5 wt % or more, 10 wt % or more, 20 wt % or more, 30 wt % or more, 40 wt % or more, 50 wt % or more, 60 wt % or more, 70 wt % or more, 80 wt % or more, or 90 wt % or more. As another exemplary embodiment, a content of the extract may be 100 wt % or less, 90 wt % or less, 80 wt % or less, 70 wt % or less, 60 wt % or less, 50 wt % or less, 40 wt % or less, 30 wt % or less, 20 wt % or less, 10 wt % or less, 5 wt % or less, or 3 wt % or less.

In an aspect, a dosage of the active ingredient may be 5 mg/kg/day to 1000 mg/kg/day based on the dry weight. As an exemplary embodiment, the dosage may be 5 mg/kg/day or more, 10 mg/kg/day or more, 30 mg/kg/day or more, 50 mg/kg/day or more, 70 mg/kg/day or more, 100 mg/kg/day or more, 120 mg/kg/day or more, 150 mg/kg/day or more, 180 mg/kg/day or more, 200 mg/kg/day or more, 250 mg/kg/day or more, 300 mg/kg/day or more, 350 mg/kg/day or more, 400 mg/kg/day or more, 500 mg/kg/day or more, 600 mg/kg/day or more, 700 mg/kg/day or more, 800 mg/kg/day or more, or 900 mg/kg/day or more. As another exemplary embodiment, the dosage may be 1000 mg/kg/day or less, 900 mg/kg/day or less, 800 mg/kg/day or less, 700 mg/kg/day or less, 600 mg/kg/day or less, 500 mg/kg/day or less, 450 mg/kg/day or less, 400 mg/kg/day or less, 350 mg/kg/day or less, 300 mg/kg/day or less, 250 mg/kg/day or less, 200 mg/kg/day or less, 180 mg/kg/day or less, 150 mg/kg/day or less, 100 mg/kg/day or less, 50 mg/kg/day or less, 20 mg/kg/day or less, 10 mg/kg/day or less, or 8 mg/kg/day or less. When the dosage is out of the above range, the desired effect of the composition may not be achieved, or a dramatic effect that the body cannot handle may occur.

In an aspect, an administration route of the composition may be an oral administration.

In another aspect, the lipid metabolism disorders may be caused by any one selected from the group consisting of obesity, hyperlipidemia, and fatty liver.

In still another aspect, the lipid metabolism disorders may be caused by one or more selected from the group consisting of body weight gain, an increase in fat tissue weight, an increase in fat in liver tissue, an increase in triglyceride in blood, and an increase in fat tissue inflammation. According to an aspect of the present invention, it was confirmed that a green tea extract with an increased specific ingredient content remarkably suppressed body weight gain, which is caused by a remarkable decrease in fat tissue weight, remarkably suppressed an increase in triglyceride in blood, effectively reduced fat in liver tissue, and remarkably alleviated fat tissue inflammation response, compared to existing green tea extracts (see the following experimental examples).

In yet another aspect, the lipid metabolism disorders may be caused by an increase in monocyte chemoattractant protein-1 (MCP-1) expression or inflammation in fat tissue. As an exemplary embodiment, the composition may increase adiponectin expression.

According to an aspect of the present invention, the green tea extract with an increased specific ingredient content remarkably suppressed the expression of MCP-1 and remarkably increased the expression of adiponectin having an anti-inflammatory efficacy, compared to existing green tea extracts. Therefore, it is possible to effectively prevent, treat, and alleviate lipid metabolism disorders (for example, obesity, body weight gain, and the like) caused by an increase in monocyte chemoattractant protein-1 (MCP-1) expression, or inflammation in fat tissue.

In an aspect, the composition may be a food or pharmaceutical composition.

A dosage form of the food composition is not particularly limited, but the food composition may be formulated into, for example, a tablet, a granule, a pill, a powder, a liquid such as a drink, a caramel, a gel, a bar, a tea bag, or the like. For the food composition of each dosage form, ingredients typically used in the art may be appropriately selected and compounded by a person with ordinary skill in the art according to the dosage form or purpose of use in addition to the active ingredient, and when the food composition is simultaneously applied with other raw materials, a synergistic effect may occur. Further, the food may also be a health functional food.

The composition may be administered by various methods such as simple ingestion, drinking, injection administration, spray administration, or squeeze administration.

In the food composition according to an aspect of the present invention, determination of the dosage of the active ingredient is within the level of the person with ordinary skill in the art, and may vary depending on various factors such as the age, health status, and complications of the subject to be administered.

The food composition according to an aspect of the present invention may be, for example, various foods such as chewing gum, caramel products, candies, ice fruits, and confectionery, beverage products such as soft drinks, mineral water, and alcoholic beverages, and health functional foods including vitamins or minerals.

In addition to those described above, the food composition according to an aspect of the present invention may include various nutrients, vitamins, minerals (electrolytes), flavoring agents such as synthetic flavoring agents and natural flavoring agents, colorants and enhancers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like. In addition, the food compositions according to an aspect of the present invention may include flesh of fruit for the preparation of natural fruit juices and fruit juice drinks and vegetable drinks. These ingredients may be used either alone or in combinations thereof. The proportion of these additives is not significantly important, but is generally included within a range of 0 to 60 parts by weight per 100 parts by weight of the composition according to an aspect of the present invention.

The pharmaceutical composition according to an aspect of the present invention may be administered orally, parenterally, rectally, topically, transdermally, intravenously, intramuscularly, intraperitoneally, subcutaneously, and the like. Dosage forms for oral administration may be tablets, pills, soft and hard capsules, granules, powders, fine granules, solutions, emulsions or pellets, but are not limited thereto. Dosage forms for parenteral administration may be solutions, suspensions, emulsions, gels, injections, drops, suppositories, patches or sprays, but are not limited thereto. The dosage forms may be easily prepared by a typical method in the art, and may further include surfactants, excipients, wettable powders, emulsifying accelerators, suspensions, salts or buffers for controlling osmotic pressure colorants, spices, stabilizers, antiseptics, preservatives, or other equivalent adjuvants.

The composition according to an aspect of the present invention may also include a pharmaceutically acceptable salt, and the salt may include (1) acid addition salts formed by an inorganic acid such as hydrochloric acid, hydrobromic acid, sulfuric acid, nitric acid, and phosphoric acid; or an organic acid such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethane sulfonic acid, benzenesulfonic acid, 4-chlorobenzenesulfonic acid, 2-naphthalenesulfonic acid, 4-toluenesulfonic acid, camphorsulfonic acid, 4-methylbicyclo [2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid, and muconic acid; or (2) a salt formed when acidic protons present in a parent compound are substituted.

The application or dosage amount of the pharmaceutical composition according to an aspect of the present invention may vary depending on the age, sex, body weight, pathological status, and severity of the subject to be administered, administration route, or judgement of a prescriber. Determination of active ingredient dosage based on these factors is within the level of the person with ordinary skill in the art.

Another aspect of the present invention may be a method for preparing a composition for prevention or alleviation of lipid metabolism disorders, the method including: (1) adjusting moisture in green tea and inoculating one or more strains selected from the group consisting *Saccharomyces* sp., *Lactobacillus* sp., *Bacillus* sp., and *Leuconostoc mesenteroides* sp. to the green tea; (2) maintaining the inoculated green tea at 40 to 60° C.; (3) aging the inoculated green tea at 70 to 80° C.; and (4) adding one or more of water and C1 to C6 alcohols thereto and extracting a green tea extract at 50° C. to 80° C.

Still another aspect of the present invention may be a method for maximizing a content of (−)-gallocatechin gallate (GCG) in a green tea extract, the method including: (1) adjusting moisture in green tea and inoculating a *Bacillus* genus strain to the green tea; (2) maintaining the inoculated green tea at 40 to 60° C.; (3) aging the inoculated green tea at 70 to 80° C.; and (4) adding one or more of water and C1 to C6 alcohols thereto and extracting a green tea extract at 50° C. to 80° C.

In an aspect, the strain in step (1) may be one or more selected from the group consisting of *Saccharomyces cerevisiae, Lactobacillus casei, Bacillus subtlis, Lactobacillus bulgarius*, and *Leuconostoc mesenteroides*.

In an exemplary embodiment, the strain may be a strain obtained from the food microorganism gene bank of Korea Food Research Institute, or a strain owned by other research institutions or a commercially available strain, and specifically, may be a strain selected from *Saccharomyces cerevisiae* (ATCC9763), *Lactobacillus casei* (KFRI000127), *Bacillus* subtlis (F4041, F4163), *Lactobacillus bulgarius* (KFRI000344), and *Leuconostoc mesenteroides* (KFRI818).

As another exemplary embodiment, the green tea may be used by adding water, when dried green tea leaves, for examples, dried leaves having a moisture content of less than 5 wt % are used, to the dried leaves. In an aspect, the water may be added such that the content of moisture is 20 wt % or more, 25 wt % or more, 30 wt % or more, 35 wt % or more, 40 wt % or more, 50 wt % or more, or 60 wt % or more based on the total weight of green tea leaves to which water is added. In another aspect, the water may be added such that the content of moisture is 70 wt % or less, 65 wt % or less, 60 wt % or less, 50 wt % or less, 45 wt % or less, 35 wt % or less, or 30 wt % or less. Within the above range, the activity of the strain may be enhanced, and the uniform quality maintenance and processing easiness of green tea leaves may be enhanced. When the content of moisture is less than the above range, it may be difficult to maintain the uniform quality of green tea leaves, and when the content of moisture is more than the above range, green tea leaves may adhere to each other to cause a problem in the processing process, which may cause a change in ingredients of a final product.

In another aspect, the maintenance time in step (2) may be 12 hours to 120 hours. As an exemplary embodiment, the time may be 12 hours or more, 24 hours or more, 28 hours or more, 32 hours or more, 34 hours or more, 36 hours or more, 40 hours or more, 48 hours or more, 50 hours or more, 60 hours or more, 80 hours or more, or 100 hours or more. As another exemplary embodiment, the time may be 120 hours or less, 100 hours or less, 80 hours or less, 60 hours or less, 50 hours or less, 48 hours or less, 40 hours or less, 36 hours or less, 34 hours or less, 32 hours or less, 28 hours or less, 24 hours or less, or 18 hours or less.

In still another aspect, the aging time in step (3) may be 24 to 60 hours. As an exemplary embodiment, the aging time may be 24 hours or more, 26 hours or more, 28 hours or more, 30 hours or more, 32 hours or more, 34 hours or more, 36 hours or more, 40 hours or more, 42 hours or more, 44 hours or more, 46 hours or more, 48 hours or more, 50 hours or more, 52 hours or more, 54 hours or more, 56 hours or more, or 58 hours or more. As another exemplary embodiment, the aging time may be 60 hours or less, 58 hours or less, 56 hours or less, 54 hours or less, 52 hours or less, 50 hours or less, 48 hours or less, 46 hours or less, 44 hours or less, 42 hours or less, 40 hours or less, 38 hours or less, 36 hours or less, 34 hours or less, 32 hours or less, 30 hours or less, 28 hours or less, or 26 hours or less.

As an exemplary embodiment, one or more of the maintenance time in step (2) and the aging time in step (3) may be determined while tracking the content of GCG or CG.

When the time is out of the above maintenance and aging time ranges, an extract having an ingredient composition according to an aspect of the present invention may not be prepared.

In an aspect, the temperature in step (2) may be 40° C. or more, 42° C. or more, 44° C. or more, 45° C. or more, 48° C. or more, 50° C. or more, 52° C. or more, 54° C. or more, 55° C. or more, 57° C. or more, or 58° C. or more. In another aspect, the temperature in step (2) may be 60° C. or less, 58° C. or less, 56° C. or less, 54° C. or less, 52° C. or less, 50° C. or less, 48° C. or less, 46° C. or less, 44° C. or less, or 42° C. or less. When the temperature is out of the above range, it may be difficult to sufficiently extract the ingredient or the extracted component may be denatured.

As an exemplary embodiment, the temperature in step (3) may be 70° C. or more, 72° C. or more, 74° C. or more, 76° C. or more, or 78° C. or more. As another exemplary embodiment, the temperature in step (3) may be 80° C. or less, 78° C. or less, 76° C. or less, 74° C. or less, or 72° C. or less. When the temperature is out of the above range, it may be difficult to sufficiently extract the ingredient or the extracted component may be denatured.

As an exemplary embodiment, the temperature in step (4) may be 50° C. or more, 52° C. or more, 54° C. or more, 56° C. or more, 58° C. or more, 60° C. or more, 62° C. or more, 64° C. or more, 66° C. or more, 68° C. or more, 70° C. or more, 72° C. or more, 74° C. or more, 76° C. or more, or 78° C. or more. As another exemplary embodiment, the temperature in step (4) may be 80° C. or less, 78° C. or less, 76° C. or less, 74° C. or less, 72° C. or less, 70° C. or less, 68° C. or less, 66° C. or less, 64° C. or less, 62° C. or less, 60° C. or less, 58° C. or less, 56° C. or less, 54° C. or less, or 52° C. or less. When the temperature is out of the above range, it may be difficult to sufficiently extract the ingredient or the extracted component may be denatured, so that the effect of a final product may be remarkably reduced.

Hereinafter, the configuration and effect of the present specification will be described in more detail with reference to the Examples, the Experimental Examples, and the Formulation Examples. However, these Examples are provided merely for helping in understanding the present specification, and the range and scope of the present specification are not limited by the following Examples.

EXAMPLES

[Example 1] Preparation of Green Tea with Maximized GCG Content

The content of moisture was adjusted to 40 wt % by adding water to green tea (dried leaves) prepared from fresh green tea (*Camellia sinensis* var. Yabukita) leaves. Here, $5 \times 10^6$ cfu/g of *Bacillus subtillis* was inoculated to the green tea leaves, and the inoculated green tea leaves were maintained at 50° C. for 3 days. Thereafter, green tea with maximized GCG content was prepared by aging the inoculated green tea leaves at 80° C. for 36 to 48 hours. A green tea extract with maximized GCG content (yield 32%) was obtained by adding 1,000 ml of a 50% (v/v) aqueous ethanol solution to 100 g of the green tea and performing extraction under reflux at 60° C. for 3 hours. However, the method is an example, and any method can be applied as long as the method is a preparation method for maximizing the content of GCG.

In order to compare the catechin contents of the fermented green tea extract, each sample was analyzed by WATERS 2695 HPLC manufactured by Alliance, and analyzed using an ODS (C18) column. The content of catechin including GCG over time maintained at 80° C. is shown in Table 1, the GCG content during this process was tracked, and the time zone in which the most amount of GCG was present was confirmed. Each numerical value in Table 1 indicates the wt % of the corresponding ingredient, based on the total weight ratio of the extract.

TABLE 1

| Time | EGCG | GCG | ECG | CG |
|---|---|---|---|---|
| 0 h | 16.88 | — | 2.7 | — |
| 12 h | 14.03 | 0.77 | 2.39 | — |
| 24 h | 7 | 2.49 | 0.78 | 0.19 |
| 36 h | 2.08 | 3.12 | 0.42 | 0.36 |
| 48 h | 2 | 2.92 | 0.38 | 0.31 |
| 60 h | 1.86 | 2.51 | 0.33 | 0.27 |

(The ECG in the table is epicatechin 3-O-gallate)

As a result, it could be seen that the result was optimal within 36 to 48 hours, and it was confirmed that the GCG content was remarkably reduced when 5 days were elapsed. It was shown that the extract contained remarkably lower EGCG content (2.08%) and total catechin content (7.44%) than the general green tea extract, whereas GCG in a non-epimer form which was not present in the general green tea extract was produced. Accordingly, it can be said that the content of the specific component (GCG) is increased by the process, and the ingredient composition of the green tea extract with an increased specific ingredient (GCG) content is completely different from that of the green tea extract.

As a result of confirming other ingredients based on when the content of GCG in the green tea extract with an increased specific ingredient (GCG) content was 1 to 5 wt %, the total catechin, the EGCG, and the CG were shown to be 10 wt % or less, 0.8 to 4 wt %, and 0.1 to 0.5 wt %, respectively.

For the comparison of efficacy, the green tea extract according to the general preparation method (for example, a notified green tea extract according to the health functional food standards and specifications) was analyzed under the same conditions. In order to compare the contents of ingredients of the green tea extract with an increased specific ingredient content with the general tea extract, each sample was analyzed by WATERS 2695 HPLC manufactured by Alliance, and analyzed using an ODS (C18) column. These analysis results are shown in the following Table 2. The numerical values in the following table are wt % (w/w) of the corresponding ingredient based on the total weight of the extract. In the case of the green tea extract with an increased specific ingredient content, the numerical values at 36 hours in Table 1 were applied.

TABLE 2

| Composition | EGC | EC | EGCG | GCG | ECG | CG | Total catechin |
|---|---|---|---|---|---|---|---|
| Green extract with increased specific ingredient content | 1.10 | 0.36 | 2.08 | 3.12 | 0.42 | 0.36 | 7.44 |
| General tea extract | 10.57 | 3.05 | 18.45 | — | 2.88 | — | 34.95 |

(EGC is epigallocatechin, EC is (—)epicatechin, and ECG is epicatechin 3-O-gallate)

It could be seen that the extract with an increased specific ingredient content contained remarkably lower EGCG content (2.08 wt %) and total catechin content (7.44 wt %) than the general green tea extract, whereas GCG in a non-epimer form which was not present in the general green tea extract was produced. Accordingly, it can be said that the ingredient composition of the green tea extract with an increased specific component content is completely different from that of the green tea extract.

Figure 7:
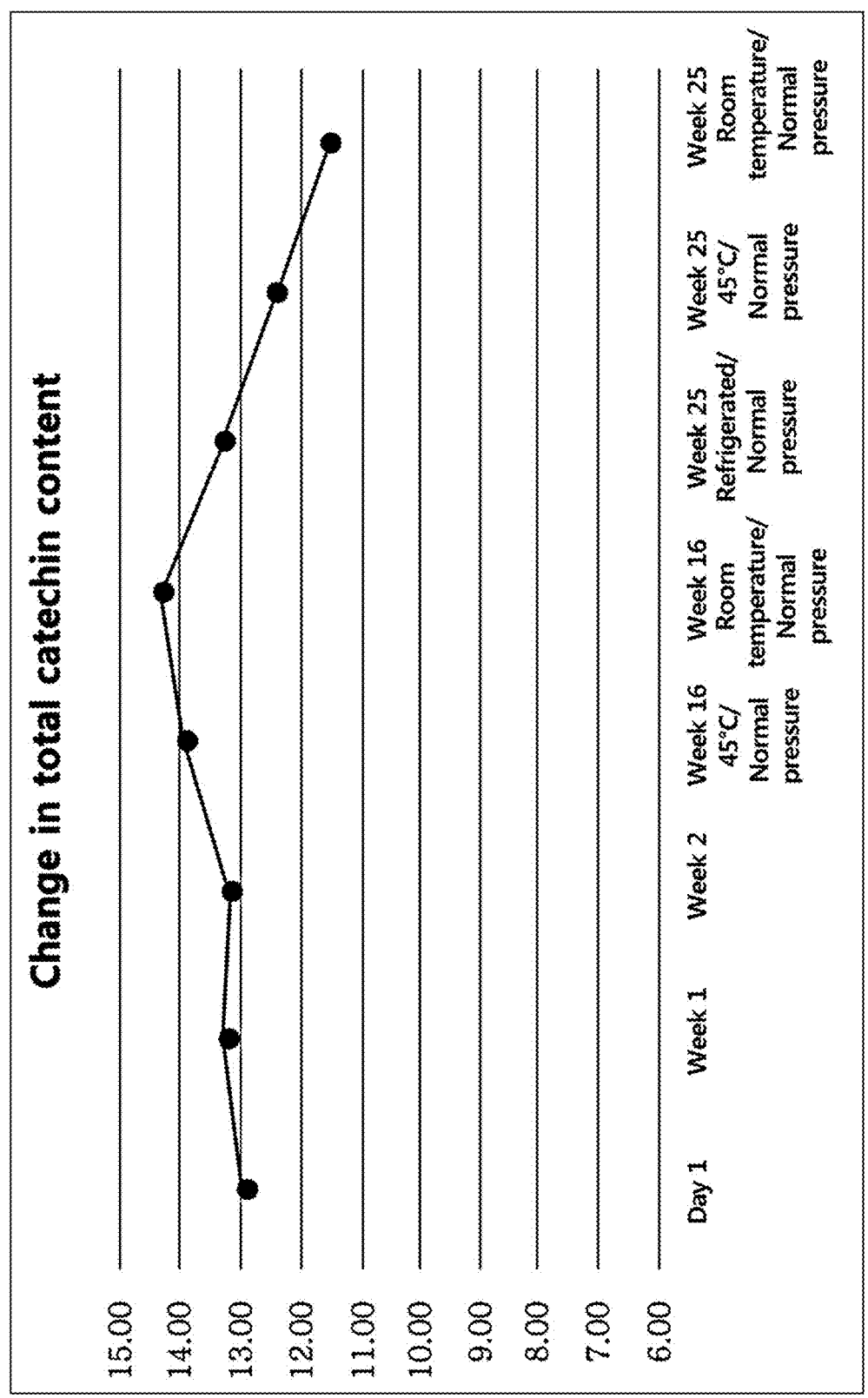
FIG. 7 illustrates the changes in total catechin content in a green tea extract with an increased specific ingredient content according to an aspect of the present invention over each time and condition.
Figure 8:
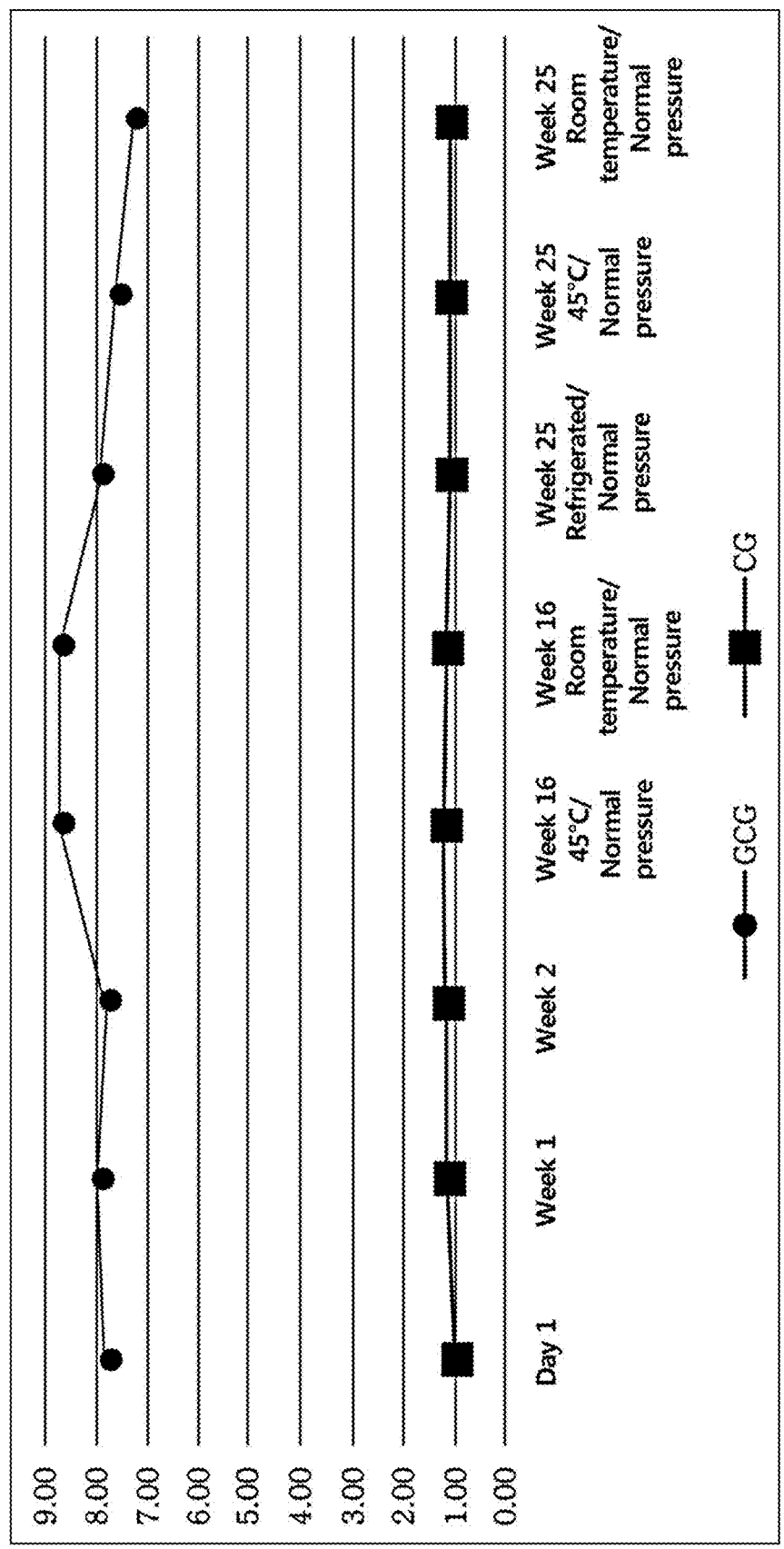
FIG. 8 illustrates the changes in content of GCG and CG in a green tea extract with an increased specific ingredient content according to an aspect of the present invention over each time and condition.

Meanwhile, as a result of evaluating the stability of each ingredient according to the conditions such as time and temperature, it could be seen that as in Table 3, the content of EGCG was rapidly decreased after a predetermined period, and thus, the total catechin content was also decreased accordingly, but GCG and CG were maintained relatively stably (see FIGS. 6 to 8).

[Experimental Example 1] Suppression of Body Weight Gain by Green Tea Extract with Increased Specific Ingredient Content The effect of suppressing the body weight gain by the green tea extract with an increased specific ingredient content obtained in Example 1 was confirmed.

Specifically, 8-week-old male C57BL/6 mice (n=9) were divided into each group and orally administered with 150 mg/kg of each of a general green tea extract and a green tea extract with an increased specific ingredient content daily for 10 weeks while being allowed to consume a high-fat diet, and the body weights were measured every week. The body weight loss was observed in the group to which the general green tea extract was administered, but it was observed that in the group to which the green tea extract with an increased specific ingredient content was administered, the rate of the body weight loss was remarkably larger than that of the group to which the general green tea extract was administered (FIG. 1).

Figure 2:
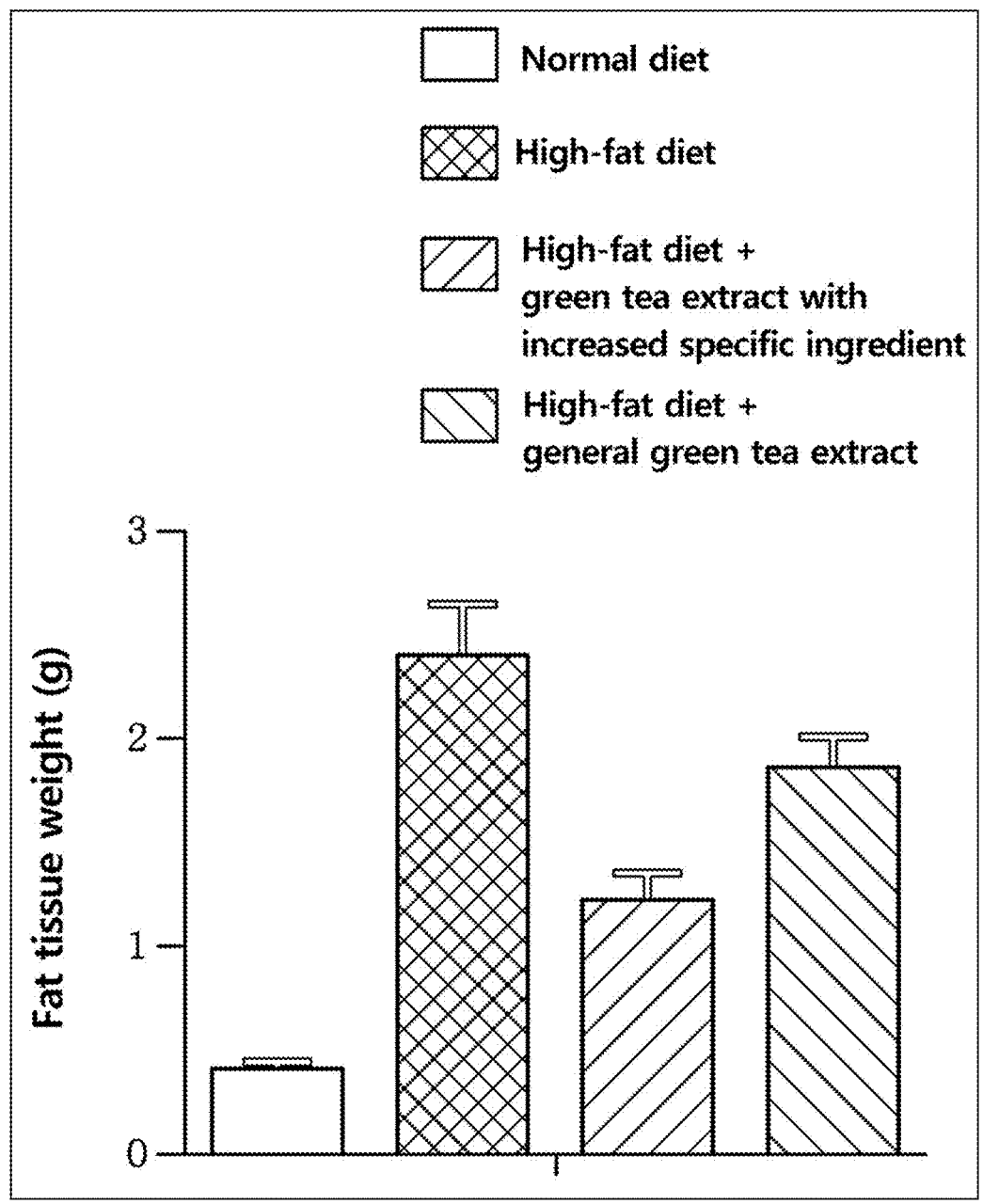
FIG. 2 illustrates the effect of a green tea extract with an increased specific ingredient content according to an aspect of the present invention on the reduction in fat tissue weight in comparison with those of other groups.

[Experimental Example 2] Reduction Effect of Fat Tissue Weight by Green Tea Extract with Increased Specific Ingredient Content An experiment was performed in the same manner as in Experiment Example 1, and ten weeks later, at the time of autopsy, the epididymis fat tissue was excised and weighed. It could be seen that the equal amount of the green tea extract with an increased specific ingredient content suppressed the increase in fat tissue weight by a high-fat diet more efficiently than the general green tea extract (FIG. 2).

[Experimental Example 3] Alleviation of Fatty Liver by Green Tea Extract with Increased Specific Ingredient Content An experiment was performed in the same manner as in Experiment Example 1, and ten weeks later, at the time of autopsy, a histopathological analysis was performed by excising the liver tissue. After the liver tissue was fixed with formaldehyde, the fat accumulated in the liver tissue was observed with H & E staining. The fat in liver tissue increased with the high-fat diet was reduced by the green tea extract with an increased specific ingredient content, mean-

TABLE 3

Figure 3:
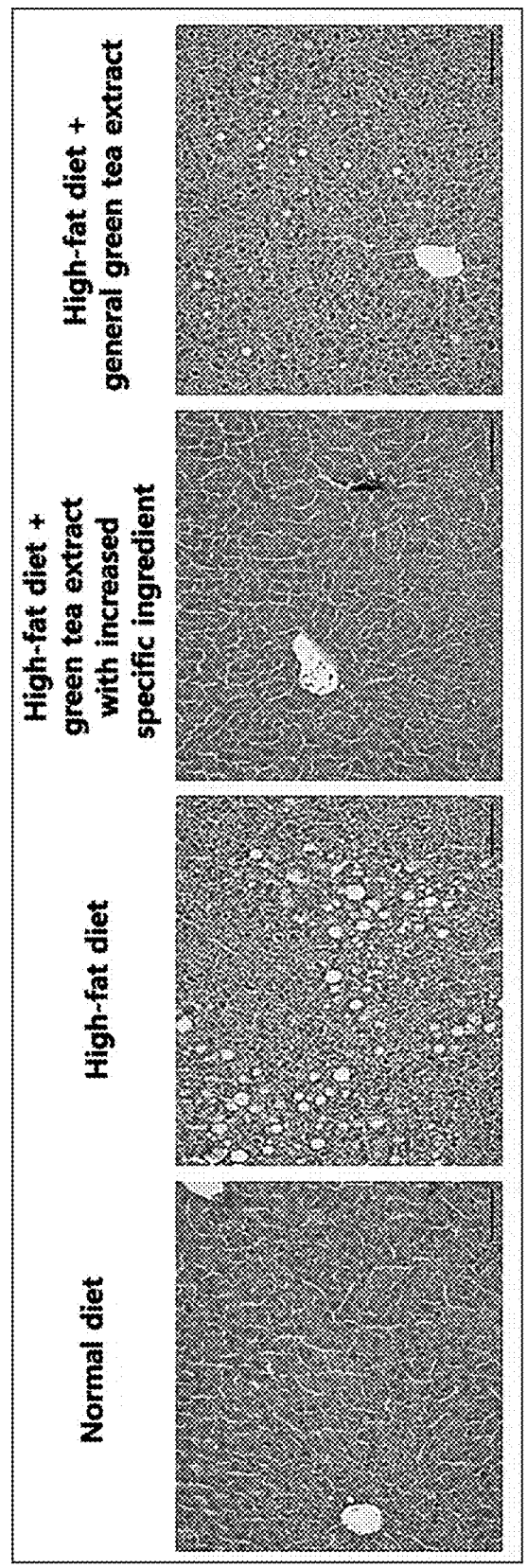
FIG. 3 illustrates the effect of a green tea extract with an increased specific ingredient content according to an aspect of the present invention on the alleviation of fatty liver in comparison with those of other groups.

| Classification | Test date | EGC | EC | EGCG | ECG | Catechin total | GCG | CG |
|---|---|---|---|---|---|---|---|---|
| Day 1 | Feb. 20, 2017 | 2.12 | 1.13 | 7.48 | 2.22 | 12.95 | 7.80 | 1.04 |
| Week 1 | Feb. 27, 2017 | 2.12 | 1.15 | 7.70 | 2.28 | 13.26 | 7.95 | 1.20 |
| Week 2 | Mar. 6, 2017 | 2.19 | 1.20 | 7.53 | 2.27 | 13.19 | 7.79 | 1.19 |
| Week 16: 45° C./Normal pressure | Jun. 14, 2017 | 2.50 | 1.32 | 7.72 | 2.38 | 13.92 | 8.74 | 1.22 |
| Week 16: Room temperature/Normal pressure | Jun. 14, 2017 | 2.84 | 1.32 | 7.79 | 2.36 | 14.31 | 8.72 | 1.21 |
| Week 25: Refrigerated/Normal pressure | Aug. 17, 2017 | 2.61 | 1.37 | 7.19 | 2.15 | 13.32 | 7.93 | 1.12 |
| Week 25: 45° C./Normal pressure | Aug. 17, 2017 | 2.28 | 1.34 | 6.61 | 2.21 | 12.44 | 7.62 | 1.13 |
| Week 25: Room temperature/Normal pressure | Aug. 17, 2017 | 2.06 | 1.32 | 6.19 | 2.02 | 11.58 | 7.27 | 1.11 |
| Standard deviation | | 0.28 | 0.09 | 0.58 | 0.12 | 0.84 | 0.51 | 0.06 | ing that the efficacy of suppressing fatty liver was better than that of the equal amount of the general green tea extract (FIG. 3).

Figure 4:
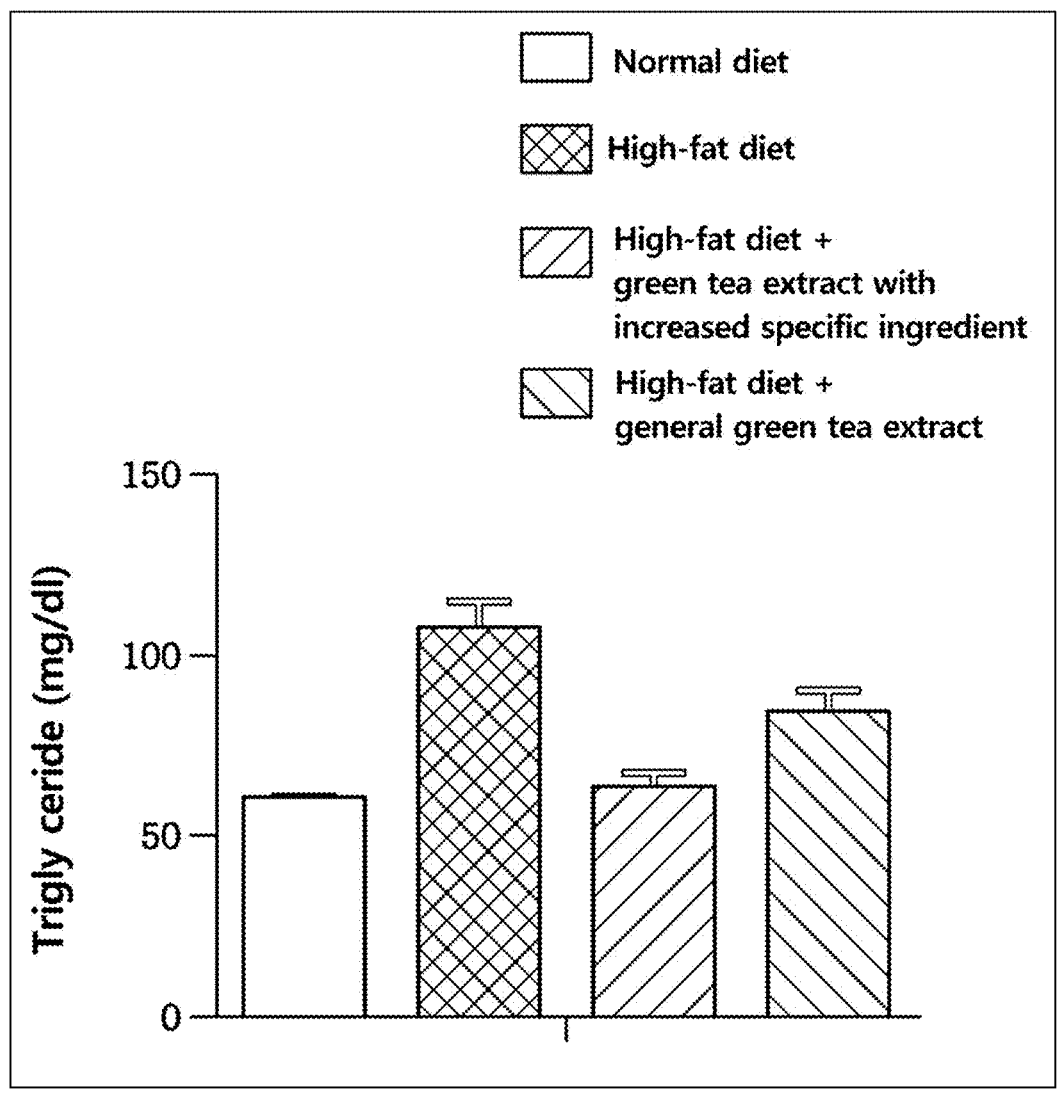
FIG. 4 illustrates the effect of a green tea extract with an increased specific ingredient content according to an aspect of the present invention on the alleviation of triglyceride in blood.

[Experimental Example 4] Alleviation of Triglyceride in Blood by Green Tea Extract with Increased Specific Ingredient Content An experiment was performed in the same manner as in Experimental Example 1, and ten weeks later, at the time of autopsy, blood was extracted, and then only blood plasma was extracted by centrifugation. As a result of measuring the level of triglyceride from the blood plasma, the green tea extract with an increased specific ingredient content suppressed an increase in triglyceride in blood caused by a high-fat diet, meaning that the efficacy was better than that of the general green tea extract (FIG. 4).

Figure 5:
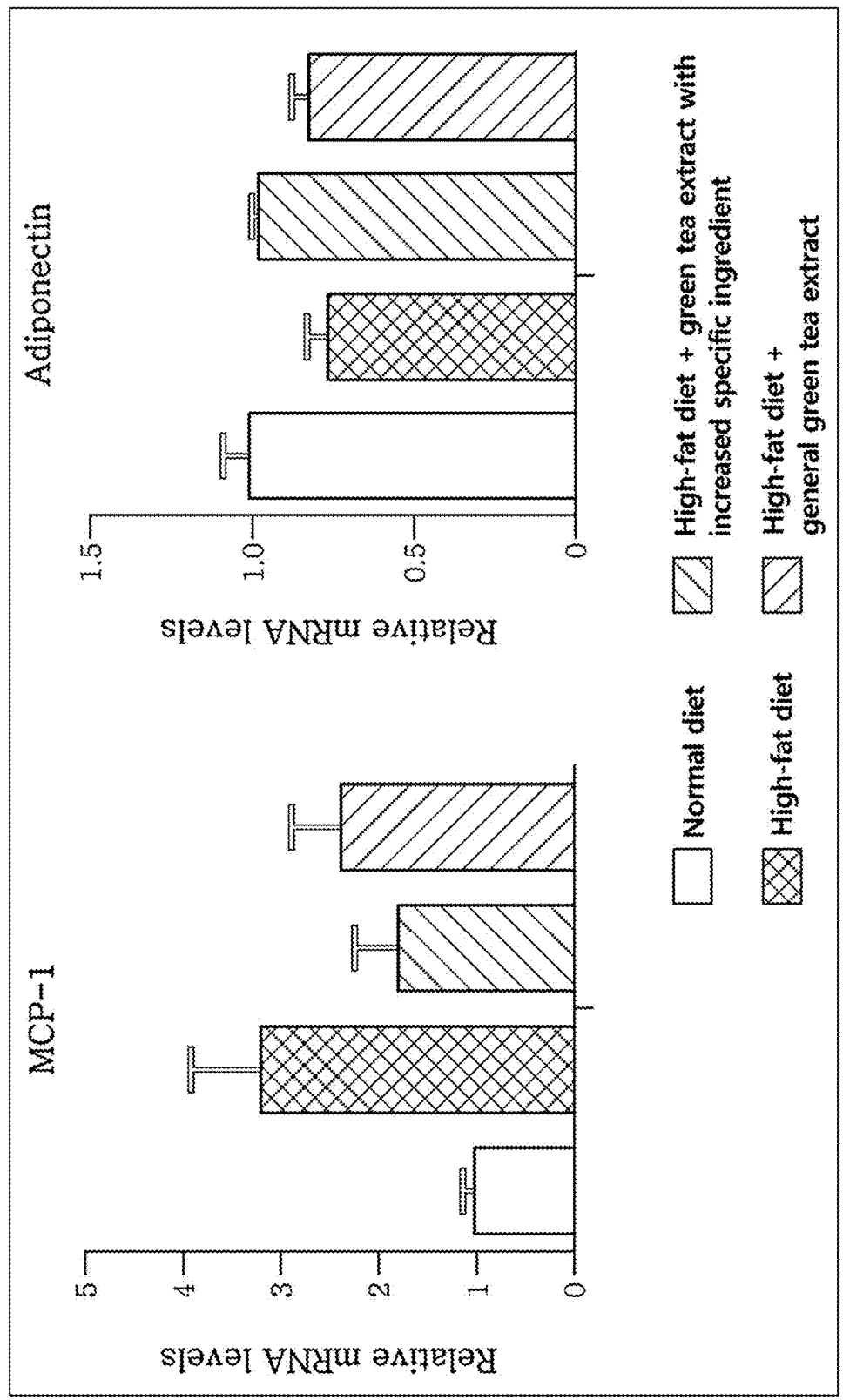
FIG. 5 illustrates the effect of a green tea extract with an increased specific ingredient content according to an aspect of the present invention on the alleviation of fat tissue inflammatory response.

[Experimental Example 5] Alleviation of Fat Tissue Inflammatory Response by Green Tea Extract with Increased Specific Ingredient Content An obesity-induced increase in fat tissue is accompanied by an inflammatory response to fat tissue, which has been pointed out as an important factor for causing metabolic diseases such as obesity. An experiment was performed in the same manner as in Experimental Example 1, and ten weeks later, the expression of cytokine related to inflammatory response in fat tissue was measured by performing an autopsy. The expression of MCP-1, which is an inflammatory secretion substance increased by a high-fat diet, was reduced by the green tea extract with an increased specific ingredient content, and the expression of adiponectin with reduced anti-inflammatory efficacy was increased. Further, it was observed that the efficacy was better than that of the existing general green tea extract (FIG. 5).

[Formulation Example 1] Soft Capsules 150 mg of an extract with an increased specific ingredient was prepared according to Example 1, and a soft capsule filling solution was prepared by mixing 150 mg of the extract with 440 mg of lactose, 430 mg of corn starch, and 2 mg of magnesium stearate. Moreover, apart from the soft capsule filling solution, soft capsule sheets were prepared at a ratio of 66 parts by weight of gelatin, 24 parts by weight of glycerin, and 10 parts by weight of a sorbitol solution, and soft capsules were prepared by filling the soft capsule sheets with the filling solution.

[Formulation Example 2] Tablets 150 mg of the extract with an increased specific ingredient was prepared according to Example 1 and mixed with 15 mg of Vitamin E, 15 mg of Vitamin C, 250 mg of galactooligosaccharide, 60 mg of lactose, and 140 mg of maltose, and then the resulting mixture was granulated using a fluidized bed dryer, and then 8 mg of sugar ester was added thereto. The composition was tableted by a typical method, thereby preparing tablets.

[Formulation Example 3] Drink 80 mg of the extract with an increased specific ingredient was prepared according to Example 1 and mixed with 9 mg of Vitamin E, 9 mg of Vitamin C, 10 g of glucose, 0.6 g of citric acid, and 25 g of liquid oligosaccharide, and then the resulting mixture was filled by adding 400 ml of purified water thereto. After a bottle was filled with the filled mixture, a drink was prepared by sterilizing the bottle at 30° C. for 4 to 5 seconds.

[Formulation Example 4] Granules 150 mg of the extract with an increased specific ingredient was prepared according to Example 1 and mixed with 9 mg of Vitamin E, 9 mg of Vitamin C, 250 mg of anhydrous crystalline glucose, and 550 mg of starch, and then the resulting mixture was molded into granulated particles using a fluidized bed granulator, and then granules were prepared by filling a pouch with the granulated particles.

[Formulation Example 5] Health Food 150 mg of the extract with an increased specific ingredient was prepared according to Example 1 and combined with a vitamin mixture (70 μg of Vitamin A acetate, 1.0 mg of Vitamin E, 0.13 mg of Vitamin B1, 0.15 mg of Vitamin B2, 0.5 mg of Vitamin B6, 0.2 μg of Vitamin B12, 10 mg of Vitamin C, 10 μg of biotin, 1.7 mg of nicotinic acid amide, and 50 μg of folic acid) and a mineral mixture (1.75 mg of ferrous sulfate, 0.82 mg of zinc oxide, 25.3 mg of magnesium carbonate, 15 mg of monopotassium phosphate, 55 mg of dicalcium phosphate, 90 mg of potassium citrate, 100 mg of calcium carbonate, and 24.8 mg of magnesium chloride) to prepare a health food.

[Formulation Example 6] Health Beverage 50 mg of the extract with an increased specific ingredient was prepared according to Example 1, and 900 mL of a health beverage was prepared by adding 1,000 mg of citric acid, 100 g of oligosaccharide, 2 g of Japanese apricot concentrate, 1 g of taurine, and the remaining amount of purified water thereto.

The invention claimed is:

1. A method for preventing and/or alleviating lipid metabolism disorders, the method comprising: administering, to a subject, a composition containing a green tea extract, as an active ingredient, comprising 1 to 5 wt % of (−)-gallocatechin gallate (GCG), 0.1 to 0.5 wt % of (−)-catechin gallate (CG), and 0.8 to 4 wt % of (−)-epigallocatechin gallate (EGCG) based on a total weight of the composition,
wherein the preventing and/or alleviating lipid metabolism disorders is preventing inflammation of fat tissue by increasing the expression of adioponectin.

2. The method of claim 1, wherein a weight ratio of EGCG:GCG in the extract is 2:1.5 to 5.

3. The method of claim 1, wherein a weight ratio of GCG:CG in the extract is 1:0.05 to 0.3.

4. The method of claim 1, wherein the extract is extracted one or more times by at least one of water, a C1 to C6 alcohol, and a mixture thereof.

5. The method of claim 1, wherein a content of the extract in the composition is 1 wt % to 100 wt % based on the dry weight.

6. The method of claim 1, wherein a dosage of the active ingredient is 5 mg/kg/day to 1000 mg/kg/day.

7. The method of claim 1, wherein an administration route of the composition is an oral administration.

8. The method of claim 1, wherein the lipid metabolism disorders are caused by any one selected from the group consisting of obesity, hyperlipidemia, and fatty liver.

9. The method of claim 1, wherein the lipid metabolism disorders are caused by one or more selected from the group consisting of body weight gain, an increase in fat tissue weight, an increase in fat in liver tissue, an increase in triglyceride in blood, and an increase in fat tissue inflammation.

10. The method of claim 1, wherein the lipid metabolism disorders are caused by an increase in MCP-1 expression or inflammation in fat tissue.

11. The method of claim 1, wherein the composition increases adiponectin expression.

12. The method of claim 1, wherein the composition is a food or pharmaceutical composition.

\* \* \* \* \*